United States Patent
Lee

(10) Patent No.: US 9,737,381 B2
(45) Date of Patent: Aug. 22, 2017

(54) DESKTOP THREE-DIMENSIONAL SCANNER FOR DENTAL USE PROVIDED WITH TWO-AXIS MOTION UNIT IN WHICH CAMERA AND PROJECTOR ARE COUPLED TO UNIT FOR CHANGING HORIZONTAL AXIS OF ROTATION OF STAGE

(71) Applicant: DOF INC., Seoul (KR)

(72) Inventor: Youngjong Lee, Seoul (KR)

(73) Assignee: DOF INC., Seoul (KR)

( * ) Notice: Subject to any disclaimer, the term of this patent is extended or adjusted under 35 U.S.C. 154(b) by 318 days.

(21) Appl. No.: 14/404,514

(22) PCT Filed: May 24, 2013

(86) PCT No.: PCT/KR2013/004550
§ 371 (c)(1),
(2) Date: Nov. 28, 2014

(87) PCT Pub. No.: WO2013/180423
PCT Pub. Date: Dec. 5, 2013

(65) Prior Publication Data
US 2015/0109424 A1    Apr. 23, 2015

(30) Foreign Application Priority Data

Jun. 1, 2012 (KR) .................. 10-2012-0059086

(51) Int. Cl.
*H04N 13/02* (2006.01)
*A61C 9/00* (2006.01)
*G01B 11/24* (2006.01)

(52) U.S. Cl.
CPC .............. *A61C 9/006* (2013.01); *G01B 11/24* (2013.01); *H04N 13/0275* (2013.01)

(58) Field of Classification Search
CPC ................................ A61C 9/006; G01B 11/24
(Continued)

(56) References Cited

U.S. PATENT DOCUMENTS 5,251,156 A    10/1993  Heier et al.
5,369,490 A  * 11/1994  Kawai .................. G01B 11/24
                                                              356/601
(Continued)

FOREIGN PATENT DOCUMENTS

EP    0 600 800    6/1994
EP    2 312 268    4/2011
(Continued)

OTHER PUBLICATIONS

Extended European Search Report(EESR),Dec. 16, 2015, European Patent Office, European patent application No. EP13797028.1.

*Primary Examiner* — Thai Tran
*Assistant Examiner* — Jose Mesa
(74) *Attorney, Agent, or Firm* — Lex IP Meister, PLLC

(57) ABSTRACT

In a desktop three-dimensional scanner for dental use of the related art, a two-axis rotation motion unit, on which a target object can be placed and rotated in order to image the entire shape of the target object, is coupled to the scanner, and thus, when a subject is placed on the imaging stage and is rotated along the horizontal axis of rotation of the stage, the subject is dropped from the stage by gravity after being inclined, and accordingly, additional fixing means or a receiving jig should be placed on the stage together with the subject to prevent same. In such a case, inconvenience is caused because the target objects to be scanned have various shapes and the fixing means or receiving jigs should fit the shapes thereof. According to one embodiment of the desktop three-dimensional scanner for dental user of the present invention, a camera and a projector are provided on the unit for changing the horizontal axis of rotation of the imaging stage, and thus a target object does not have to be inclined during the scanning process and dental prostheses of various shapes (Continued)

can be three-dimensionally scanned even without additional fixing means or a receiving jig.

3 Claims, 3 Drawing Sheets

(58) Field of Classification Search
USPC .......................................................... 348/50
See application file for complete search history.

(56)    References Cited

U.S. PATENT DOCUMENTS

2003/0202691 A1    10/2003  Beardsley
2012/0062557 A1*    3/2012  Dillon .................... A61C 7/002
                                                                    345/419

FOREIGN PATENT DOCUMENTS

| KR | 10-2007-0023601 | 2/2007 |
| KR | 10-2011-0127950 | 11/2011 |
| KR | 10-2012-0038762 | 4/2012 |
| WO | 02/16865 | 2/2002 |

* cited by examiner

DESKTOP THREE-DIMENSIONAL SCANNER FOR DENTAL USE PROVIDED WITH TWO-AXIS MOTION UNIT IN WHICH CAMERA AND PROJECTOR ARE COUPLED TO UNIT FOR CHANGING HORIZONTAL AXIS OF ROTATION OF STAGE

TECHNICAL FIELD

The present invention relates to a three-dimensional scanner, three-dimensional measurement, and CAD/CAM.

BACKGROUND ART

A three-dimensional (3D) scanner is a device used to collect numerical data with respect to a shape of a target object. The collected numerical data may be used to implement a digital 3D model. There are a plurality of technical methods to implement such 3D scanner, and each technique method has advantages and disadvantages in the aspect of technique and cost. In case of a desktop three-dimensional scanner for dental use configured to scan a target object having a comparatively small size, such as a dental replica, an optical method is usually used, and products coupled to a two-axis motion unit for scanning an entire shape of a target object, are widely used. The present invention is related to a method capable of effectively implementing a two-axis motion unit of a desktop three-dimensional scanner for dental use.

In a desktop three-dimensional scanner for dental use of the related art, a two-axis rotation motion unit, on which a target object can be placed and rotated in order to image the entire shape of the target object, is coupled to the scanner, and thus, when a subject is placed on the imaging stage and is rotated along the horizontal axis of rotation of the stage, the subject is dropped from the stage by gravity after being inclined, and accordingly, additional fixing means or a receiving jig should be placed on the stage together with the subject to prevent same. In such a case, inconvenience is caused because the target objects, such as dental prostheses, to be scanned by a desktop three-dimensional scanner for dental use, have various shapes and the fixing means or receiving jigs should fit the shapes thereof. According to the desktop three-dimensional scanner for dental user of the present invention, a camera and a projector are provided on the unit for changing the horizontal axis of rotation of the imaging stage, and thus a target object does not have to be inclined during the scanning process and various shapes can be three-dimensionally scanned even without additional fixing means or a receiving jig.

DISCLOSURE OF THE INVENTION

Therefore, an object of the present invention is to provide a desktop three-dimensional scanner for dental use, capable of having no additional fixing means or fixing jig by preventing a target object from being inclined during a scanning process, by having a rotation motion unit which can be rotated by 360° along a vertical rotation axis of an imaging stage in order to capture a target object to be scanned, from every angle except for a bottom surface, and by providing a camera and a projector on a rotation motion unit which can be rotated by 90° along a horizontal rotation axis of the imaging stage.

The present invention can have the following advantages.

A desktop three-dimensional scanner for dental use is used to scan various dental prostheses such as dental replicas and dental molds. The conventional desktop three-dimensional scanner for dental use has to be used together with an additional fixing means or receiving jig for fixing a target object on a stage, against a case where a target object to be scanned such as dental prostheses is inclined to drop from an imaging stage when the target object placed on the imaging stage is captured while being rotated two-dimensionally. However, when a target object to be scanned is dental prostheses, the target object cannot be fixed by such additional fixing means or fixing jig due to their various shapes. In this case, the only solution is to provide the target object with a plurality of additional fixing jigs for respective cases. However, the plurality of fixing jigs for precise scanning may cause high costs, because they should have accuracy. On the other hand, the desktop tree-dimensional scanner for dental use according to the present invention can be substantially used with considerably reduced costs, since additional fixing means or fixing jig is not required according to a target object to be scanned.

MODES FOR CARRYING OUT THE PREFERRED EMBODIMENTS

Figure 1:
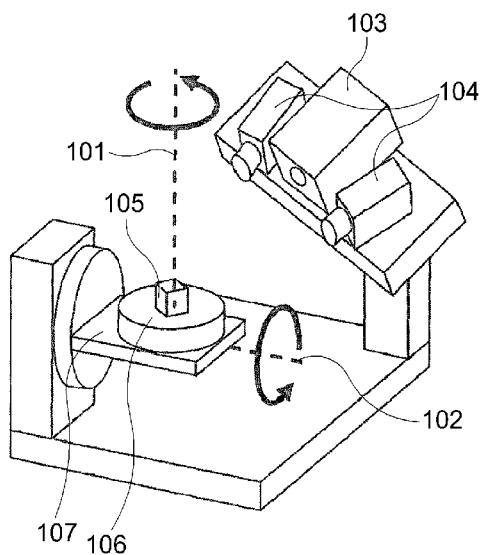
FIG. 1 is a view illustrating a structure of a desktop three-dimensional scanner for dental use in accordance with the conventional art.

Preferred embodiments of the present invention will be described below in detail with reference to the accompanying drawings where the same components are provided with the same reference numerals even if they are shown in different figures. In describing the present invention, if a detailed explanation for a related known function or construction is considered to unnecessarily divert the gist of the present invention, such explanation has been omitted but would be understood by those skilled in the art.

A three-dimensional (3D) scanner is a device used to collect numerical data with respect to a shape of a target object, and to implement a digital 3D model through the collected numerical data. There are a plurality of technical methods to implement such 3D scanner, and each technique method has advantages and disadvantages in the aspect of technique and cost. In the field of dentistry, widely used are desktop three-dimensional scanners having a size large enough for dental replicas, dental molds, etc. to be placed on a desk for scanning. Such desktop three-dimensional scanner for dental use is generally provided with a two-axis rotation motion unit perpendicular to each other, because an object to be scanned should be captured from every angle for implementation of a digital 3D model.

FIG. 1 is a view illustrating a structure of a desktop three-dimensional scanner for dental use in accordance with the conventional art. In the conventional desktop three-dimensional scanner, a target object to be scanned 105 is placed on an imaging stage 106, and scanning pattern light is irradiated onto the target object to be scanned 105, from a projector 103, from every angle except for a bottom surface of the target object to be scanned 105, by rotating the target object 105 along a vertical rotation axis 101 perpendicular to the imaging stage, and a horizontal rotation axis 102 parallel to the imaging stage. Then scanning pattern images are captured by a camera 104 to obtain data. The obtained data is used to perform a three-dimensional recombination algorithm, so that a digital three-dimensional (3D) model can be implemented. The conventional desktop three-dimensional scanner is coupled to a two-axis motion unit for rotating the imaging stage 106 on which the target object to be scanned 105 is placed along the vertical rotation axis 101 and the horizontal rotation axis 102. In this case, an error occurring when a rotation motion is controlled is less influential on entire accuracy after scanning, since a rotation center is close to the target object to be scanned. However, the target object to be scanned may be inclined to drop from the imaging stage, because the imaging stage on which the target object is placed should be rotated along the horizontal rotation axis. Accordingly, a method of fixing the target object to be scanned to the imaging stage is required. Generally, used are fixing jigs for fixing a target object to be scanned using pincers having elasticity, while fixing the target object to be scanned to an imaging stage. However, in this case, a shape of the pincers of the fixing jigs should be variable according to a shape of a target object to be scanned. Accordingly, fixing jigs of various shapes should be additionally provided. However, such fixing jigs cause high costs, since high accuracy and high quality are required for accuracy of three-dimensional scanning. This results in high costs in providing a plurality of fixing jigs of various shapes.

Figure 2:
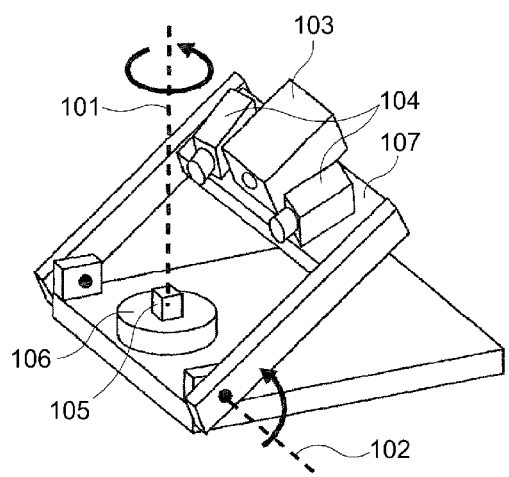
FIG. 2 is a view illustrating a structure of a desktop three-dimensional scanner for dental use according to an embodiment of the present invention, the structure where a projector and a camera are provided on a unit for changing a horizontal axis of rotation of stage.

In order to solve the problem, the present invention provides a structure. FIG. 2 is a view illustrating a structure of a desktop three-dimensional scanner for dental use according to an embodiment of the present invention, the structure where a projector and a camera are provided on a unit for changing a horizontal axis of rotation of stage. Unlike the conventional desktop three-dimensional scanner for dental use, in the desktop three-dimensional scanner for dental use according to the present invention, a target object to be scanned 105, placed on an imaging stage 106, has only to be rotated along a vertical rotation axis 101, in case of capturing the target object to be scanned 105 from every angle except for a bottom surface of the target object 105, with rotating the target object 105 along a horizontal rotation axis 102 parallel to the imaging stage. The reason is because capturing can be performed in a state where a projector 103 for irradiating scanning pattern light and a camera 104 move together on a unit 107 for changing a horizontal axis of rotation of stage. As a result, the target object to be scanned 105 does not drop from the imaging stage 106. This does not require fixing means or a fixing jig for fixing the target object to be scanned 105 to the imaging stage 106.

Figure 3:
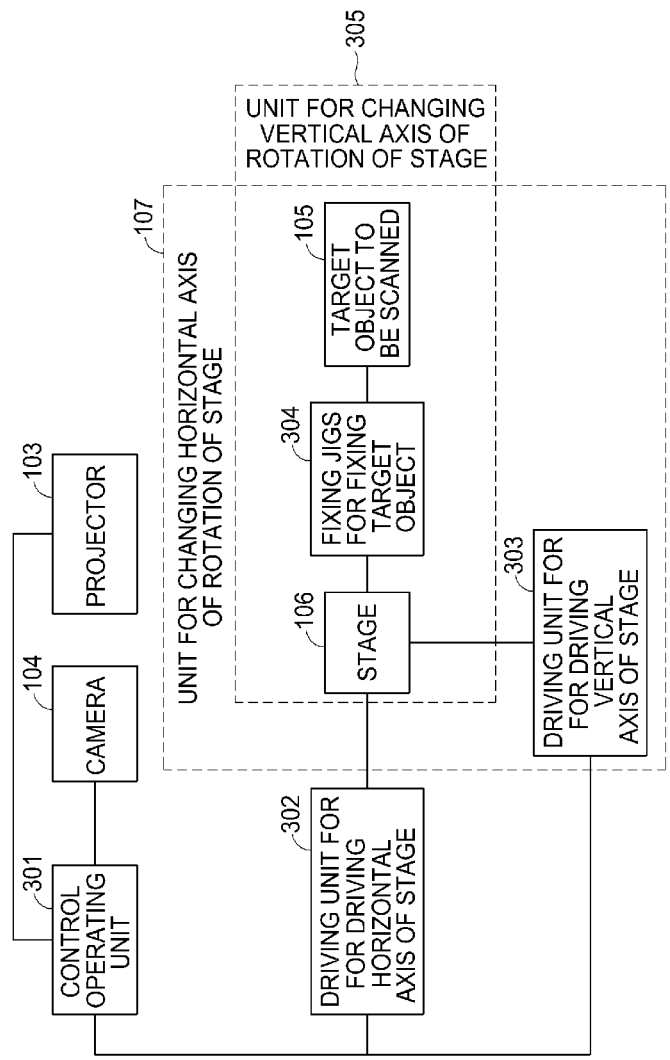
FIG. 3 is a block diagram illustrating a desktop three-dimensional scanner for dental use in accordance with the conventional art.

FIG. 3 is a block diagram illustrating a desktop three-dimensional scanner for dental use in accordance with the conventional art. In the conventional desktop three-dimensional scanner for dental use, a unit 305 for changing a vertical axis of rotation of stage, which is rotated along a vertical rotation axis of stage, includes a target object to be scanned 105, a fixing jig 304 for fixing the target object to be scanned on a stage 106, and the stage 106 on which the target object 105 is placed. The unit 107 for changing a horizontal axis of rotation of stage, which is rotated along a horizontal rotation axis of stage, includes the unit 305 for changing a vertical axis of rotation of stage, and a driving unit 303 for driving a vertical axis of rotation of stage. The unit 107 for changing a horizontal axis of rotation of stage is driven by a driving unit 302 for driving a horizontal axis of rotation of stage, and a control operating unit 301 controls the driving unit 302 for driving a horizontal axis of rotation of stage, and the driving unit 303 for driving a vertical axis of rotation of stage, thereby rotating the stage along each axis. The control operating unit 301 irradiates scanning pattern light onto the target object to be scanned, through a projector 103. And the control operating unit 301 implements a three-dimensional digital model of the target object, through a three-dimensional scan modeling algorithm, based on image data obtained, from a camera 104, by capturing images formed as the scanning pattern light has been irradiated onto the target object.

Figure 4:
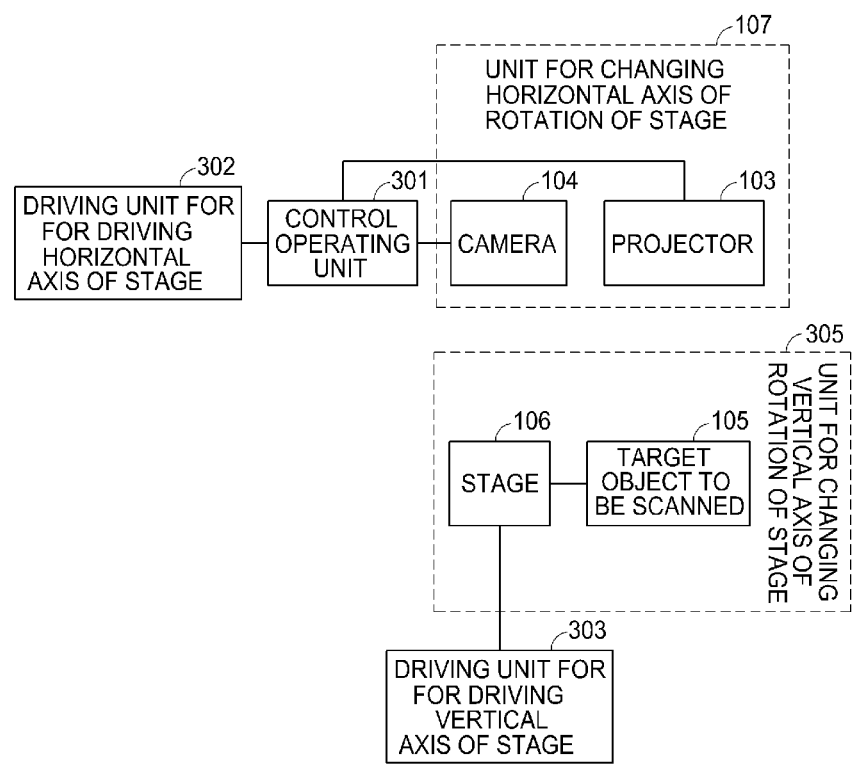
FIG. 4 is a block diagram of a desktop three-dimensional scanner for dental use according to an embodiment of the present invention, the structure where a projector and a camera are provided on a unit for changing a horizontal axis of rotation of stage.

FIG. 4 is a block diagram of a desktop three-dimensional scanner for dental use according to an embodiment of the present invention, the structure where a projector and a camera are provided on a unit for changing a horizontal axis of rotation of stage. In the desktop three-dimensional scanner for dental use according to an embodiment of the present invention, a unit 305 for changing a vertical axis of rotation of stage, which is rotated along a vertical rotation axis of stage, includes a target object to be scanned 105, and a stage 106 on which the target object 105 is placed. A unit 107 for changing a horizontal axis of rotation of stage, which is rotated along a horizontal rotation axis of stage, includes a camera 104 and a projector 103. A control operating unit 301 controls a driving unit 302 for driving a horizontal axis of rotation of stage, and a driving unit 303 for driving a vertical axis of rotation of stage, thereby rotating the unit 107 for changing a horizontal axis of rotation of stage, and the unit 305 for changing a vertical axis of rotation of stage. The control operating unit 301 irradiates scanning pattern light onto the target object to be scanned 105, through the projector 103. And the control operating unit 301 implements a three-dimensional digital model of the target object, through a three-dimensional scan modeling algorithm, based on image data obtained, from the camera 104, by capturing images formed as the scanning pattern light has been irradiated onto the target object.

In the present invention, the camera and the projector are provided on the unit for changing a horizontal axis of rotation of stage. Under such configuration, the stage on which the target object to be scanned is placed does not have to be inclined for capturing of the target object from every angle. This can allow additional fixing means or fixing jigs not to be required.

It will also be apparent to those skilled in the art that various modifications and variations can be made in the present invention without departing from the spirit or scope of the invention. Thus, it is intended that the present invention cover modifications and variations of this invention provided they come within the scope of the appended claims and their equivalents.

The invention claimed is:

1. A desktop three-dimensional scanner for dental use, comprising:
   a camera;
   a projector;
   a mounting base on which the camera and the projector are mounted;
   a stage;
   a control operator;

a first axis motion driver driving the mounting base to rotate about a horizontal rotation axis; and a second axis motion driver driving the stage to rotate about a vertical rotation axis, wherein the mounting base is installed to be rotatable around the horizontal rotation axis which is parallel to an upper surface of the stage, wherein the first axis motion driver is independently provided from the second axis motion driver, thereby the rotation about the vertical rotation axis of the stage capable of being simultaneously performed with the rotation about the horizontal rotation axis of the mounting base, and wherein the control operator is configured to control the camera, the projector, the first axis motion driver and the second axis motion driver to rotate the mounting base while irradiating scanning pattern light onto a target object to be scanned which is provided on the stage, through the projector and to implement a three-dimensional digital model of the target object.

2. The desktop three-dimensional scanner for dental use of claim 1, wherein the projector is configured to irradiate visible rays.

3. The desktop three-dimensional scanner for dental use of claim 1, wherein the projector is configured to irradiate laser beams.

* * * * *